US00PP36975P3

(12) United States Plant Patent
Childs et al.

(10) Patent No.: US PP36,975 P3
(45) Date of Patent: Sep. 23, 2025

(54) ELDERBERRY PLANT NAMED 'WCE'

(50) Latin Name: *Sambucus canadensis*
Varietal Denomination: WCE

(71) Applicants: Daniel Childs, Hinsdale, NY (US); Carrie Childs, Hinsdale, NY (US)

(72) Inventors: Daniel Childs, Hinsdale, NY (US); Carrie Childs, Hinsdale, NY (US)

( * ) Notice: Subject to any disclaimer, the term of this patent is extended or adjusted under 35 U.S.C. 154(b) by 0 days.

(21) Appl. No.: 18/445,818

(22) Filed: Feb. 20, 2024

(65) Prior Publication Data

US 2025/0268113 P1 Aug. 21, 2025

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226, 156
CPC ..... A01H 5/02; A01H 5/00; A01H 5/08
See application file for complete search history.

*Primary Examiner* — Kent L Bell
(74) *Attorney, Agent, or Firm* — HUESCHEN AND SAGE

(57) ABSTRACT

A new and distinct variety of elderberry plant 'WCE' selected to provide a fruit which is firmer and sweeter in taste than the fruit of known cultivars and wild elderberry plants known to the Inventors. Compared to other wild and commercial cultivars known to the Inventors, the present invention yields clusters of berries which will consistently ripen 99% of the fruits within every fruit raceme.

7 Drawing Sheets

Latin name: *Sambucus canadensis.*
Variety denomination: Elderberry plant named 'WCE'.

BACKGROUND OF THE INVENTION

Elderberry plants are perennial flowering plants with ripe purple berries. Elderberries are rich in antioxidants and anthocyanidins that give elderberry juice an intense purple coloration. Various commercial products which are derived from elderberries include nutritional/dietary supplements, food/juice/beverage products, as well as natural colorant compositions.

The present invention is a new and distinct variety of elderberry plant specifically suited to the commercial trade. It is reminiscent of other named elderberry cultivars known to the Inventors producing acceptable quality, flavorful fruits, and high plant vigor. Compared to other named cultivars, the elderberry plant named 'WCE' bears large clusters of very deep purple berries, and exhibits concentrated fruit ripening of fruit clusters and fruit clusters grown on a shorter statured plant height unlike elderberry cultivars known to the Inventors. Compared with other wild and commercial cultivars known to the Inventors, the elderberry plant of the present invention yields clusters of berries which will consistently ripen 99% of the fruits within every fruit raceme. Ripened fruits exhibit a hot pink, bright purple color juice. The elderberry fruit of 'WCE' is sweeter than the fruit of other elderberry plants known to the Inventors. The fresh berries of 'WCE' are sweeter, having a sugar content of 16 degrees Brix and higher compared to other cultivars known to the Inventors which have a sugar content of 12 degrees Brix or lower.

BRIEF SUMMARY OF THE INVENTION

This invention concerns a new and distinct elderberry plant designated: 'WCE', having a botanical name of *Sambucus canadensis*. Elderberry plant 'WCE' provides one or more advantages compared to the parental and/or other elderberry varieties known to the Inventors. For example, elderberry plant 'WCE' exhibits a high chilling requirement, fine berry quality, early ripening of fruits, disease resistance to phytophthera, stem blight, and stem blotch, reasonable insect resistance to, for example, Ericoid Mites and Japanese Beetles, and is cold tolerant to minus 26 degrees Fahrenheit (F) (minus 31 degrees Celsius (C)). Elderberry plant 'WCE' provides for harvest of 99% of ripe fruits in 3 separate harvest times.

Elderberry plant 'WCE' is characterized by its free flowering without the use of growth regulating chemicals, fine berry quality, yields of uniform ripening of 99% ripe fruits, acceptable resistance to fungal infections, acceptable resistance to insect pests, and ripens uniformly with no more than 1% unripe fruits at the time of harvest.

The fruits of elderberry plant 'WCE' yield a quality juice described as a hot pink, bright purple color.

The fresh berries and juice of elderberry plant 'WCE' are described as being sweet, with aromas of blackberry and mulberry.

Elderberry plant 'WCE' was derived from an open-pollination of unnamed parents from a native germplasm collection of wild elderberry plants which were growing commercially in Humphrey Township, Hinsdale, New York USA in 1999. Elderberry plant 'WCE' was discovered and selected in a cultivated area in Humphrey Township, Hinsdale, New York USA in September 2018 for its unusual and specific characteristics, and testing of the 'WCE' variety proceeded from that date until the present. Elderberry plant 'WCE' was selected for cold weather tolerance and survivability to fluctuating winter temperatures of −20° F. to −26° F. Compared to other wild and commercial cultivars known to the Inventors, the present invention yields clusters of berries which will consistently ripen 99% of the fruits within every fruit raceme.

The Elderberry plant 'WCE' was asexually propagated in a cultivated area during the 2014 growing season in Hinsdale, New York USA and in Grand Junction, Michigan USA utilizing conventional hardwood cuttings, softwood cuttings and in-vitro methods. The plants so propagated have shown the unique features of this new *Sambucus canadensis* variety named 'WCE' and are stable and reproduce true to type in successive generations of asexual propagation.

The description of the new and distinct variety of elderberry plant 'WCE' based on its flower, fruit, stems, and foliage is based on observations of specimens grown in Humphrey Township, Hinsdale, New York USA. Fruits of elderberry plant 'WCE' exhibit late summer fruiting and begin ripening September first, in Western New York USA, one week before the commercial elderberry cultivars 'Johns' and 'Adams'. The fruits begin ripening over a 14 week period after pollination of flowers.

Elderberry plant 'WCE' yields large deep colored purple berries on large racemes. Elderberry plant 'WCE' is a five feet (1.52 meters) tall, multi-stemmed shrub. The plant spreads outward approximately 2 to 3 feet. The plant has a high chilling requirement, minimum of 700 accumulative chilling hours between temperatures 32° to 45° F. (0° to 7° C.) which is similar to many of the *Sambucus canadensis* varieties known to the Inventors.

Elderberry plant 'WCE' fruit quality is firm with 99% of fruits ripening uniformly within the raceme. The fruits are suitable for fresh and process markets. Fresh fruits of elderberry plant 'WCE' can be stored for 21 days at temperatures 33° to 40° F. (0.5° to 4.4° C.) without deterioration compared to commercial varieties of elderberry plants, 'Johns' and 'Adams', that if stored at the same temperatures can be stored for only 12 days before deterioration.

BRIEF DESCRIPTION OF THE DRAWINGS

The accompanying photographs are of a six-year-old Elderberry plant 'WCE' grown in Hinsdale, New York USA and illustrate the overall appearance of the new and distinct variety of Elderberry plant 'WCE'.

DETAILED BOTANICAL DESCRIPTION

Figure 1:
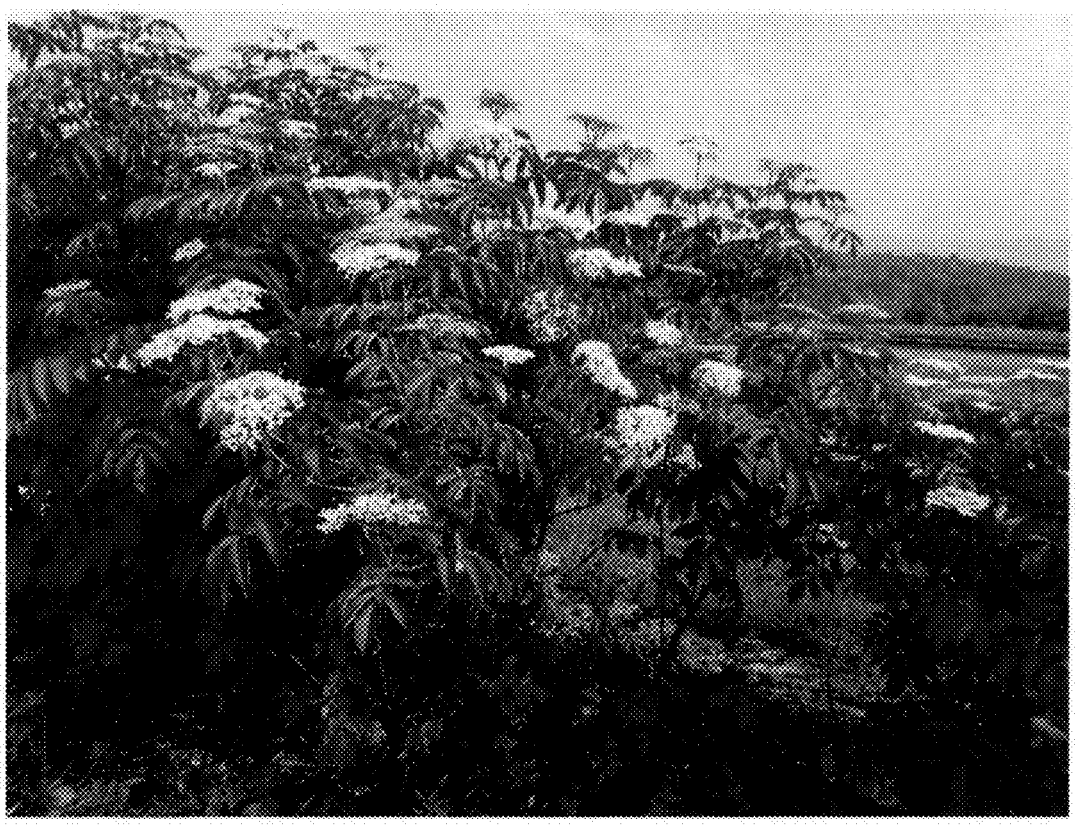
FIG. 1. A photographic illustration showing 100% open flowers and leaves of elderberry plant 'WCE'.
Figure 2:
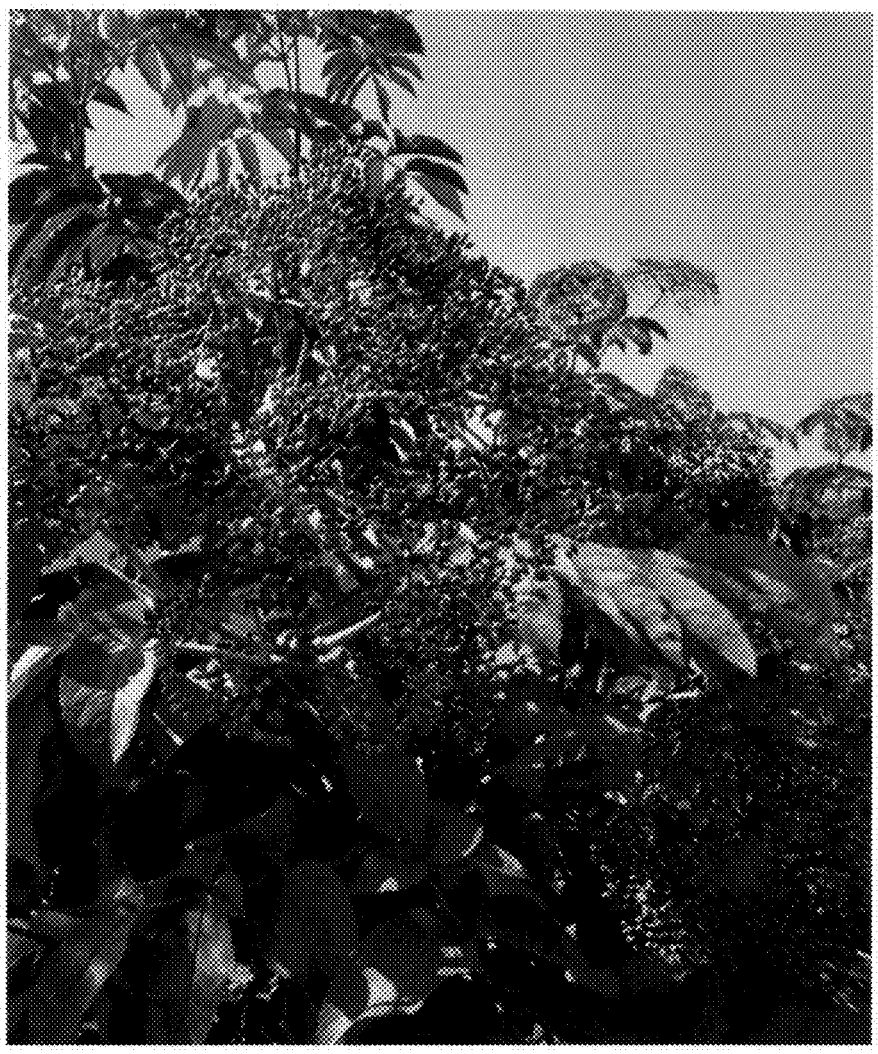
FIG. 2. A photographic illustration of the unripe fruit and leaves of elderberry plant 'WCE' including the shape, approximate color, arrangement of the cluster.
Figure 3:
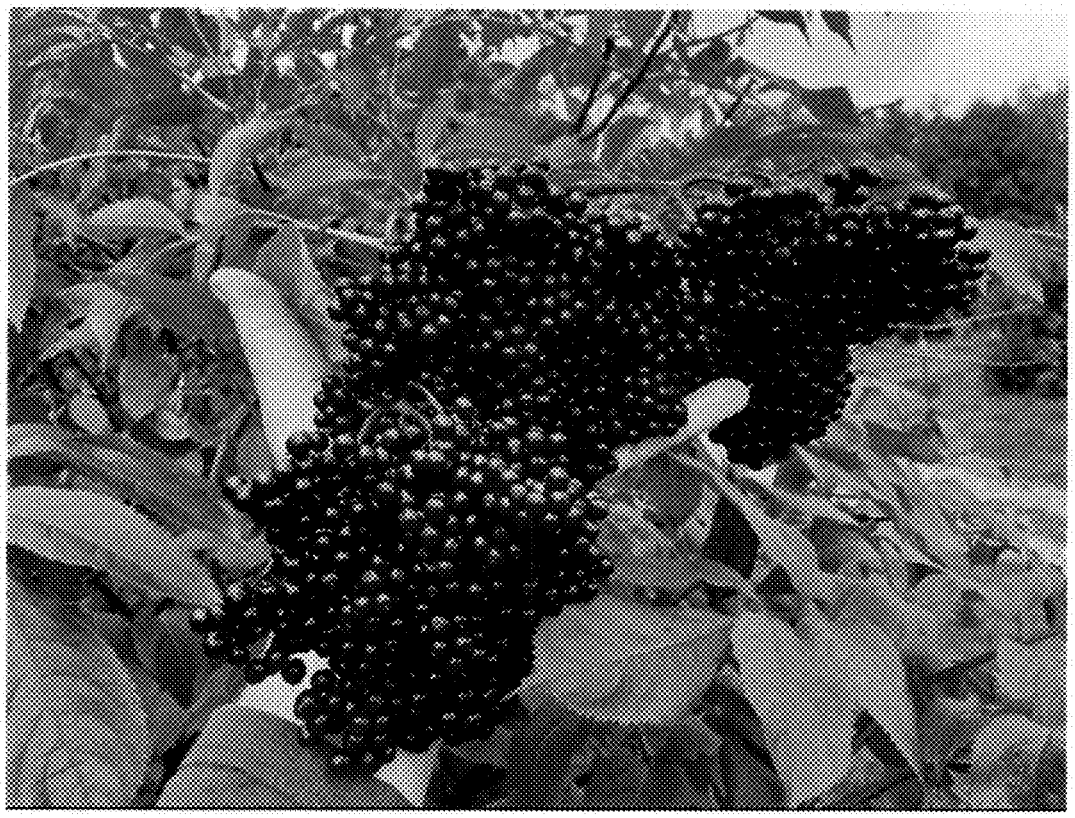
FIG. 3. A photographic illustration of elderberry plant 'WCE' fruit cluster 4 days before ripeness indicating uniform ripening of black fruits/berries.
Figure 4:
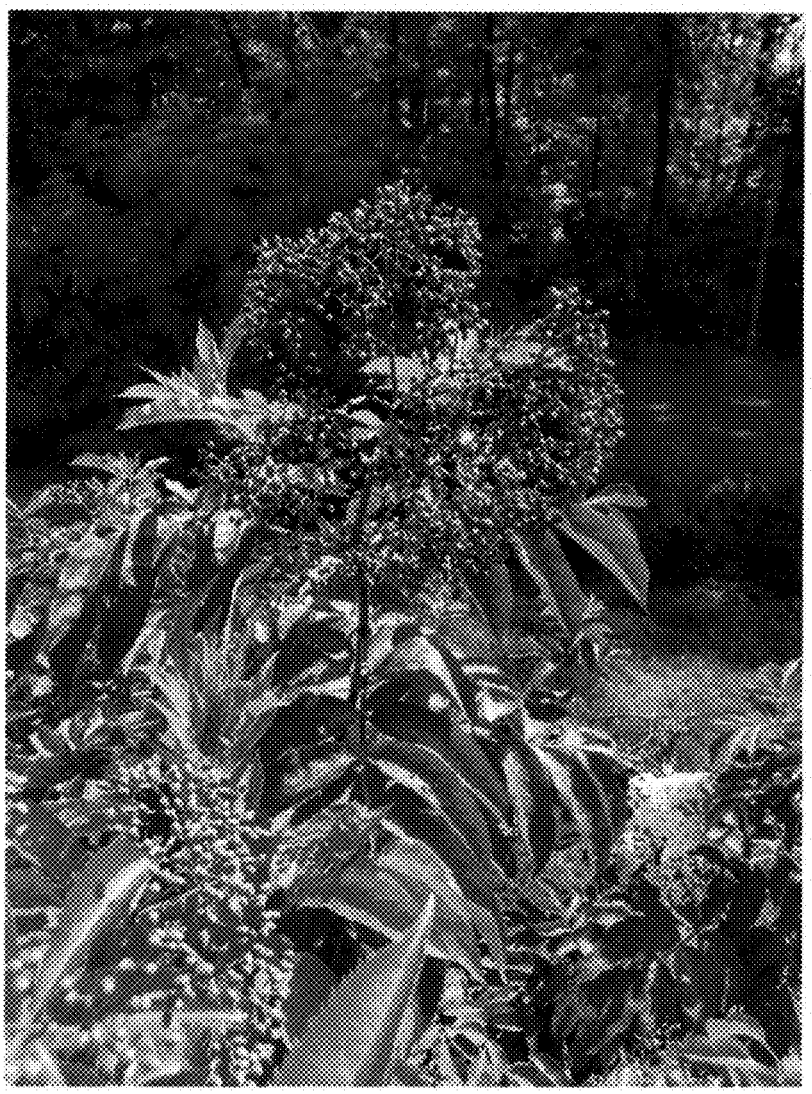
FIG. 4. A photographic illustration of the cluster of elderberry plant 'WCE' ripe fruit indicating uniform ripeness from the plant grown in Hinsdale, New York USA.
Figure 5:
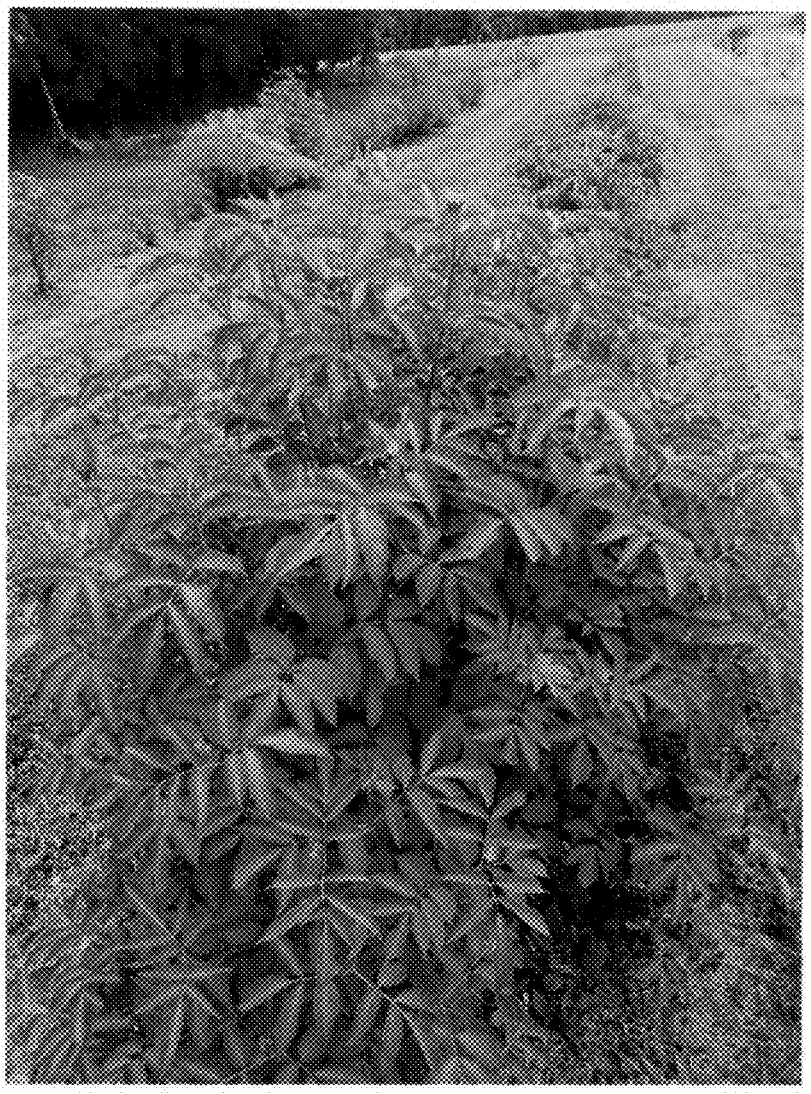
FIG. 5. A photographic illustration of the leaves and stems of the elderberry plant 'WCE' grown in Hinsdale, New York USA.
Figure 6:
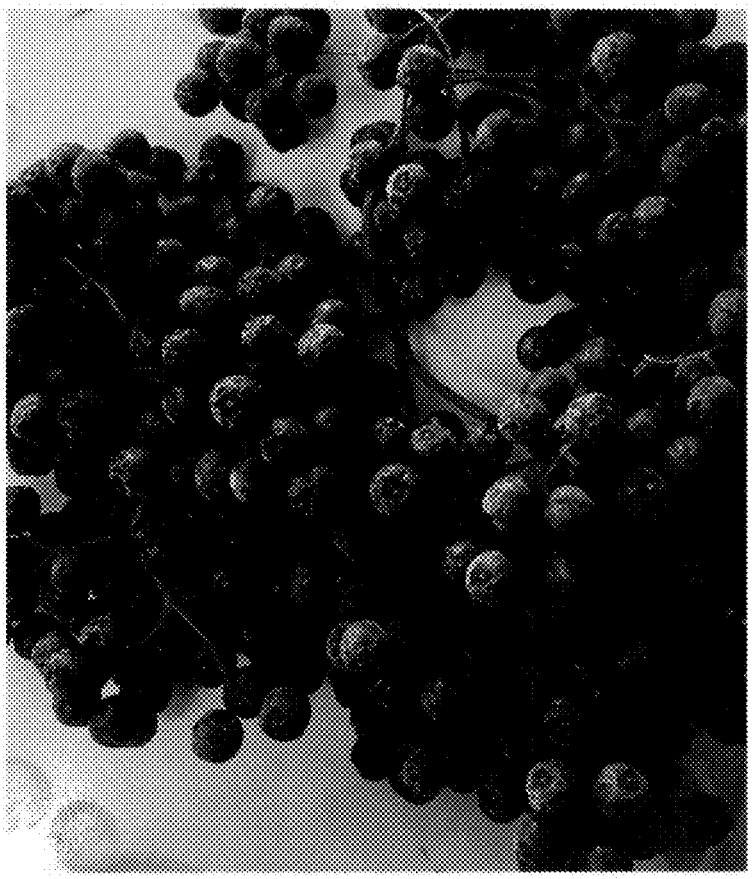
FIG. 6. A photographic illustration of elderberry plant 'WCE' fruits after they are frozen.
Figure 7:
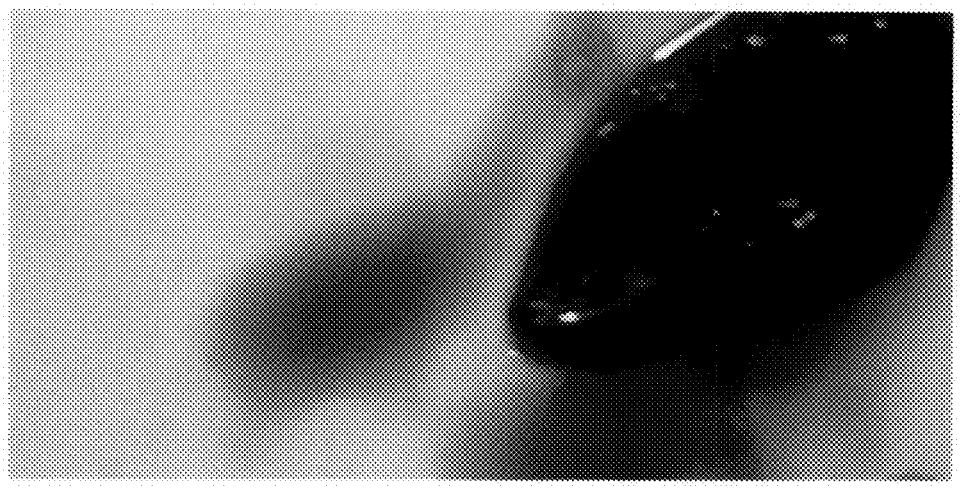
FIG. 7. A photographic illustration of juice color extracted from one fresh ripe berry of elderberry plant 'WCE'.

The following is a detailed botanical description of the new and distinct variety of elderberry plant 'WCE', including its flower, fruit, foliage, stems and habit.

Statements of characteristics herein represent exemplary observations of the cultivar herein. Where dimensions, sizes, colors, and other characteristics are given, it is to be understood that such characteristics are approximations and averages. The field observations reported herein are largely based on observations of specimens grown at Hinsdale, New York USA. The specimens were propagated from the original plant and have retained the characteristics of the original selection.

Cultivar name.-'WCE'.

Botanical name.-*Sambucus canadensis.*

Common name.-Elderberry.

Parentage: Female parent.-unnamed, native wild *Sambucus canadensis* (unpatented). Male parent.-unnamed, native wild *Sambucus canadensis* (unpatented).

The following measurements were from a mature elderberry plant 'WCE' and yielding fruits.

Color description, except those given in common terms, use designations cited from the Royal Horticulture Society (R.H.S.) color chart. (Royal Horticultural Society Colour Chart. Published by The Royal Horticultural Society, 80 Vincent Square. London, UK SW1P 2PE 2001 Edition). Where the color designation cited in RHS charts differ from the color shown in the drawings the color cited from the R.H.S. charts should be considered accurate. Any deviation from those colors in the drawings is due to failure of photographic process to exactly duplicate the colors of nature.

Bush: The following measurements were from the elderberry plant 'WCE' grown for 6 years in a sandy loam soil.

*Mature height of plants.*—5 to 6 feet. Crown diameter averages 24 inches (61 cm) Suckering tendency — Yes it does sucker. Root Spread — 24 inches in diameter from the stem. Root Description — fibrous, elongated, branched with rhizomes. Root Color — shades of light brown (R.H.S. 165 to R.H.S. 167C). Root Vigor — Cold tolerant to U.S.D.A Hardiness Zone 4.

*Leaves.*—Leaf arrangement — opposite, deciduous, pinnately compound. Leaf Length — 17 to 20 cm. Leaf width — 10 to 15 cm. Leaves per lateral branch — The lateral branches grow opposite leaves every 3-4 inches along the lateral stem, averaging 3 to 7 leaves per lateral branch. Leaf type — compound. Leaflets per leaf — 5-7. Leaflets shape — lanceolate. Leaflet margin — serrated. Leaflet length — approximately 6 cm to 10 cm. Leaflet width — approximately 1.5 cm to 2 cm in the mid-section and narrowing towards the ends of the leaflet. Leaflet texture — upper and lower surfaces of leaflets with serrated edges are glaucous. Leaflet color during growing season — Upper surface varies from R.H.S. N134A to 135B. Leaflet color during growing season — Lower surface, 134B. Leaf petiole length — approximately 2.2 cm. Leaf petiole diameter — 2.4 mm. Leaf petiole color — R.H.S. 135B. Rachis length — approximately 10 cm to 17.5 cm. Rachis diameter — approximately 5 mm at the petiole and narrows to 2 mm and smaller at the apex. Rachis texture — pliable. Rachis color — R.H.S. N134B. Summer color of upper surface of leaflets — R.H.S. 139-B Summer color of bottom surface of leaflets — 138-A Autumn color of upper side of leaflets — R.H.S. 22A. Autumn color of underside of leaflets — R.H.S. 20C.

*Flowers*.—Pistil number — 1 Pistil length — less than 1 mm Ovary color — R.H.S. 141C Stamen number — 3-5 Stamen length — 2-3 mm Anther length — less than 1 mm Anther width — less than 1 mm Anther color — R.H.S. 151A Filament color — R.H.S. 17B Petal number — 5 Petal shape — oval to oblong-lanceolate lobes. Petal size — 4 mm to 5 mm wide. Petal surface — glaucous. Petal color on both surfaces — Pure White (R.H.S. N155 D) Pollen Color — (R.H.S. 10D) Pollen production per flower — Minute, 2-4 pollen grains. Flower longevity — The longevity of all flowers in each cyme is approximately 6 days. Flower fragrance — aromas of blends of sweet berries and pure honey.

*Flower type*.—Flower bracts are deciduous and glaucous. They appear when the foliage has 100% emergence, end of June in Hinsdale, New York USA. Flowers are borne on flat terminal compound cyme. Flower buds — Flower buds in the cyme are small and rounded. Flower bud diameter — 3 mm before swelling. Flower bud color — R.H.S. 142A. Flower corolla shape and size — 10.24 cm +/− 1.75 cm. Flower corolla shape — rotate with short tube; 5 petals having oval to oblong-lanceolate lobes. Corolla — Pure white Color of the fresh anthers in flower at anthesis — R.H.S. 20A. Diameter of corolla — 4 mm to 6 mm. Corolla color at anthesis — (R.H.S. 155 C) Sepal shape — typical of *Sambucus canadensis*; triangular, rounded at the top. Sepal size — less than 1 mm in length and less than 1 mm in width. Sepal surface — abaxial surface is glabrous Sepal color — typical of *Sambucus canadensis*; green (R.H.S. 135B) Calyx color at anthesis — (R.H.S. 142 C) Number of calyx lobes —5 Calyx lobes — toothed. Flowering period — The flowering period occurs in early summer, approximately the second week of July in Hinsdale, NY, for a period of 10 days. Flower inflorescence in one cyme — 180-200. Flower inflorescence longevity — the longevity of a flower inflorescence is approximately 6 days. Flower inflorescence length — 14 to 18 cm. Number of flowers per cyme — 400-480. Berry cluster — loose and open Pedicel length at unripe green fruit — 2 mm Pedicel length — 4-5 cm. Pedicel diameterm — the diameter of the stem is 4-5 mm at the base of the inflorescence. The diameter of the terminal before branching occurs is 2-4 mm. Pedicel color — (R.H.S. 142 B) Pedicel color — glaucous; R.H.S. 135B. Peduncle length at berry maturity — 2 mm. Peduncle length — 8-11 cm. Peduncle diameter — 3-4 mm. Peduncle color — glaucous; R.H.S. 135B.

*Number of berries per cyme*.—400-480. Berry weight — 3,000 to 3,100 berries per pound (453 gram) Berry width — 5 and 7 mm. Berry height — 4 mm. Berry skin color of immature fruit — R.H.S. N144C Berry skin color (with bloom on plant a day before ripening) — reddish-purple (R.H.S. 59-A) Berry skin color of ripe fruit after bloom rubbed off — dark purple (R.H.S. N77 A) at full maturity. Berry quality — Firm. Berry shape — Globose. Seeds per berry — 4 Seed size — Length — 0.2 mm — Width — 0.1 mm. Average weight +/−2,000 seed = 1 gram Color or mature seeds — R.H.S. N170-A Internal flesh color — R.H.S. 60-B Berry firmness — 5; Scale of 1-5, wherein 1 is an elderberry having the least firmness and 5 is an elderberry having the most firmness. Berry flavor — 5; Scale of 1-5, wherein 1 is an elderberry having the least desirable flavor profile and 5 is an elderberry having the most exceptional flavor profile. Berry texture — Mildly firm flesh. Mature berry Brix — 16% Typical Harvest date — The first harvest date in Hinsdale, NY occurs in the third week of August for a period of approximately two weeks. Maturity date of berry — 100% ripeness occurs September 12$^{the}$ in Hinsdale, NY USA. A day before ripening, the reddish-purple (R.H.S. 59-A) fruits change to dark purple (R.H.S. N77A) overnight for harvest 100% of the fruit clusters within several days.

*Productivity*.—yields up to 14 pounds (6.3 Kg) of berries per plant per year at plant maturity.

Plant stems are cold tolerant to minus 26 degrees F. (minus 32.2 degrees C.). Plant stem color — one and 2 year stems are colored green (R.H.S. 140 B) Fruiting stem color — Red colored (R.H.S. 60 A) Color of branches — 3 or more years — Brown (R.H.S. 176 B) and (R.H.S. 165 B). Main branch length — 5 to 6 feet. Number of main branches — 8. Habit of main branches — upright Aspect of branches — slightly spreading at the terminal to a diameter of 36 inches. Strength of the main branches — turgid to support a 2 to 4 pound fruit load on the terminal of each branch. Branch texture — smooth with an internodal length of 12 to 16 inches.

The berries are very suitable for fresh marketing and can be stored for 21 days at temperatures 33 to 40 degrees F. (0.5 to 4.4 degrees C.).

The following ratings are on a scale of 1-5, 5 is best. a. Spreading habit — 5 b. Upright — 5 c. Leaf to fruit ratio — 4 d. Time of flower — 5 e. Time of harvest — 5 f. Fruit size — 5 g. Fruit color — 5 h. Fruit Firmness — 5 i. Stem Scar — 4 j. Tightness of cluster 5 k. Foliar diseases — 4 l. Fruit rots — 5 m. Yield — 5 n. Uniform ripeness — 5

*Resistance to diseases and insects*.—a. Phytophthora — 5 b. Stem Blight (*Botrytis cortices*) — 5 c. Leaf spot (*Gloeosproium minus*) — 5 d. Stem Blotch (*Cercospora*) — 5 e. Eriophyid Mites (*Phyllocoptes wisconsinenses*) — 5 f. Japanese Beetle (*Popilla japonica*) — 2

COMPARISON WITH COMMERCIAL VARIETIES

Elderberry plant 'WCE' is most similar to 'Johns' (non-patented) and 'Adams' (non-patented). A comparison of elderberry plant 'WCE' with these two commercial varieties is as shown below.

*Characteristics of 'WCE'*.—Medium Leaflet — width 10.0-15.0 cm. Large Leaflet — length 17.0-20.0 cm. Leaflet petiole — length 4.0-4.5 cm. Leaflet margins — serrated Leaflet shape — lanceolate Top Leaflet Color — R.H.S. 139-B Bottom Leaflet Color — R.H.S. 138-A New Fruiting lateral Stem Color — R.H.S. N134 D Calyx — Smooth slightly rough. Fruit Stems Color R.H.S. N134 D Fruit Stem Length — 5.0-7.0 cm. Ripe Fruit Color — R.H.S. N77 A

*Characteristics of 'Johns'*.—Medium Leaflet length 16-18 cm. Medium Leaflet width 14-17 cm. Leaflet Petiole length 6.0 to 7.0 mm. Leaflet margins — serrated Leaflet Shape — lanceolate Top Leaflet Color — R.H.S. 137-A Bottom Leaflet color — R.H.S. 138-B New fruiting lateral stem color R.H.S. 141-C Caylx — Smooth rough Leaf Node on fruiting laterals 2.5 cm Fruit Stem Color — 141-C Berry Stem length — 3.0 mm Ripe Fruit Color — R.H.S. N92 A and R.H.S. N92 B

*Characteristics of 'Adams'*.—Medium Leaflet Length 17-20 cm. Medium Leaflet width 15-17 cm. Leaf Petiole length — 7.0 to 8.0 mm Leaflet margins — serrated Leaflet Shape — lanceolate Top Leaflet Color — R.H.S. 137 B Bottom Leaflet Color — R.H.S. 138 B New fruiting lateral stem color R.H.S. 141 C Caylx — Smoot, slightly rough Leaf node on fruiting laterals 3.0 cm Berry stem length — 3.5 to 4.0 cm Fruit stem length — 3.0 mm Ripe Fruit Color — R.H.S. N92 A and R.H.S. N92 B Rating on a 1-5 scale, 5 being the best.

*A. 'WCE' Characteristics*.—1. Upright in growth habit 5 feet tall, 3 feet wide — 5 2. Fruit quality — 5 3. Fruit size — 5 4. Yield — 5 5. Pruning moderately yearly — 5 6. Cold Tolerant — 5

*B. 'Johns' Characteristics*.—1. Upright in growth habit 6 feet tall, 4 feet wide — 4 2. Fruit quality — 3 3. Fruit size — 4 4. Yield — 4 5. Prune moderately yearly or prune as primocane — 4.5 6. Cold Tolerance — 3

*C. 'Adams' Characteristics*.—1. Upright in growth habit 6 feet tall 4 feet wide. — 4 2. Fruit quality — 4. 3. Fruit size — 4 4. Yield — 5 5. Prune moderately yearly. — 4 6. Cold Tolerant — 3

Fruit clusters of 'Johns' and 'Adams' ripen with black berries. Approximately 6 percent within the raceme being purple, red, and green berries. Compared to 'WCE' the fruit clusters of elderberry plant 'WCE' will ripen with 99% reddish-purple berries and changing overnight with 99% dark purple berries within the raceme.

Green berries within a raceme of ripe elderberries appear in all known elderberry cultivars. The green berries found mixed in with ripe black elderberry fruits in other known cultivars are difficult to sort out post-harvest. The green berries will convert to a sticky green paste within the ripe fruits when making wine, syrup, or juice which taints the end use product.

Elderberry plant 'WCE' exhibits 1% or less green berries within a raceme comprising ripe dark purple fruits making harvest easier and elderberry products of higher quality than products from existing elderberry cultivars known to the Inventors.

What is claimed is:

1. A new and distinct variety of elderberry plant named 'WCE' as illustrated and described herein.

* * * * *